(12) United States Patent
Tilley

(10) Patent No.: US 7,803,545 B2
(45) Date of Patent: Sep. 28, 2010

(54) INDUCED HETERODUPLEX GENERATORS

(75) Inventor: Louise Anne Tilley, Bristol (GB)

(73) Assignee: IHG Pharmaco Limited, London (GB)

( * ) Notice: Subject to any disclaimer, the term of this patent is extended or adjusted under 35 U.S.C. 154(b) by 67 days.

(21) Appl. No.: 11/664,908

(22) PCT Filed: Oct. 10, 2005

(86) PCT No.: PCT/GB2005/003896

§ 371 (c)(1),
(2), (4) Date: Jan. 8, 2008

(87) PCT Pub. No.: WO2006/038037

PCT Pub. Date: Apr. 13, 2006

(65) Prior Publication Data

US 2008/0187914 A1   Aug. 7, 2008

(30) Foreign Application Priority Data

Oct. 8, 2004  (GB) ................................. 0422417.6
Oct. 29, 2004 (GB) ................................. 0424103.0

(51) Int. Cl.
C12Q 1/68 (2006.01)
C07H 21/02 (2006.01)
C07H 21/04 (2006.01)

(52) U.S. Cl. ........................ 435/6; 536/23.1; 536/24.3
(58) Field of Classification Search .................. 435/6; 536/23.1, 24.3
See application file for complete search history.

(56) References Cited

FOREIGN PATENT DOCUMENTS

GB      A-2338062     12/1999
WO     WO-A-93/19201   9/1993

OTHER PUBLICATIONS

Belli et al., Rapid detect6ion of Exon 1 NRAS gene Mutations using Universal Heteroduplex Generator Technology. Human Mutation 21 : 132-137 (2003).*
Wood et al. Genetic screening and testing by induced hetyeroduplex formation. Electrophoresis 17 : 247-254 (1996).*
Belli et al., Rapid detection of exon 1 NRAS gene mutations using universal heteroduplex generator technology. Human Mutation 21 : 132-137 (2003).*
Culpan et al., Rapid mutation screening in type 2A von Willebrand's disease using universal heteroduplex generators. British J. of Haematology 96 : 464-469 (1997).*
Wood et al., Rapid classification of phenylketonuria genotypes by analysis of heteroduplexes generated by PCR-amplifiable synthetic DNA. Human Mutation 2 : 131-137 (1993).*
Pennisi, E., A closer look at SNPs suggest difficulties. Science 281 : 1787-1789 (1998).*
Smith AJP, Keen LJ, Wood NAP, Elson CJ, Bidwell JL (2004) Haplotype analysis of IL1A, IL1B, IL1RN and IL1R1 promoter SNPs. In: HLA 2002. Blackwell Munksgaard, Denmark. (Abstract).

Bidwell, JL, Clay, TM, Wood, NAP, Pursall, MC, Martin, AF, Bradley, BA and Hui, KM (1993) Rapid HLA-DR-Dw and DP matching by PCR fingerprinting and related DNA heteroduplex technologies. pp. 99-116 in: Handbook of HLA Typing Techniques [Eds KM Hui & JL Bidwell] CRC Press: Boca Raton, Florida.
Wood, N, Tyfield, L, Bidwell, J (1993) Rapid classification of phenylketonuria genotypes by analysis of heteroduplexes generated by PCR-amplifiable synthetic DNA. Human Mutation 2: 131-137.
Bidwell, JL, Wood, NAP, Tyfield, LA, Clay, TM, Culpan, D, Evans, JM, Pursall, MC, Bradley, BA (1993) Universal heteroduplex generators: reagents for genotyping of HLA and of human diseases. Molecular Bases of Human Diseases (Ed. E.E.Polli). pp. 27-34. Elsevier/North-Holland, Amsterdam.
Wood, N, Standen, G, Hows, J, Bradley, B, Bidwell, J. (1993) Diagnosis of sickle cell disease with a universal heteroduplex generator. Lancet 342: 1519-1520.
Bidwell, JL, Wood, NAP, Clay, TM, Pursall, MC, Culpan, D, Evans, J, Bradley, BA, Tyfield, LA, Standen, G, Hui, KM (1994) DNA heteroduplex technology. In: Chrambach, A, Dunn, MJ, Radola, BJ (Eds), Advances in Electrophoresis, vol. 7, pp. 311-351. VCH Press, Weinheim.
Clay, TM, Cuplan, D, Howell, WM, Sage, DA, Bradley, BA, Bidwell, JL. (1994) UHG crossmatching: a comparison with PCR-SSO typing in the selection of HLA-DPB1-compatible bone marrow donors. Transplantation 58: 200-207.
Bidwell, JL. (1994) Advances in DNA-based HLA-typing methods. Immunology Today 15: 303-307.
Tyfield, LA, Stephenson, A, Bidwell, JL, Wood, NAP, Cockburn, F, Harvie, A, Smith, I. (1994) Mutation analysis of the phenylalanine hydroxylase gene using heteroduplex analysis with synthetic DNA constructs. Acta Paediatrica 83: 47-48.
Savage, DA, Wood, NAP, Bidwell, JL, Hui, KM. (1995) HLA-DRB1*01 subtyping by heteroduplex analysis. Tissue Antigens 45: 120-124.
Wood, N, Standen, G, Murray, EW, Lillicrap, D, Holmberg, L, Peake, IR, Bidwell, J. (1995) Rapid genotype analysis in type 2B von Willebrand's disease using a universal heteroduplex generator. Brit J Haematol 89: 152-156.
Wood, N, Standen, G, Old, J, Bidwell, J. (1995) Optimisation and properties of a UHG for genotyping of haemoglobins S and C. Hum Mutation 5: 166-172.
Savage, DA, Wood, NAP, Bidwell, JL, Fitches, A, Old, JM, Hui, KM. (1995) Detection of b-thalassaemia mutations using DNA heteroduplex generator molecules. Brit J Haematol 90: 564-571.
Tyfield, LA, Zschocke, J, Stephenson, A, Cockburn, F, Harvie, A, Bidwell, JL, Wood, NAP, Hunt, LP. (1995) Discordant phenylketonuria phenotypes in one family: the relationship between genotype and clinical outcome is a function of multiple effects. J Med Genet 32: 132-136.

(Continued)

Primary Examiner—Ethan Whisenant
(74) Attorney, Agent, or Firm—Husch Blackwell Sanders LLP Welsh & Katz

(57) ABSTRACT

Heteroduplex band resolution is found to be improved by modifying the induced heteroduplex generator (IHG) molecule such that the identifier is spaced apart from the nucleotide position immediately adjacent to the site of the polymorphism which is to be genotyped. Unexpectedly, it is found that, when such modified IHG molecules are used, the resolution of the induced heteroduplexes is significantly improved.

14 Claims, 2 Drawing Sheets

OTHER PUBLICATIONS

Wood, NAP, Bidwell, JL. (1996) UHG: heteroduplex and universal heteroduplex generator analysis. In: Laboratory protocols for mutation detection (ed Landegren, U), pp. 105-112. Oxford University Press for the Human Genome Organisation.

Wood, N, Bidwell, J. (1996) Genetic screening and testing by induced heteroduplex formation. Electrophoresis 17: 247-254.

Wood, N, Standen, GR, Bowen, DJ, Cumming, A, Lush, C, Lee, R, Bidwell, J. (1996) UHG-based mutation screening in type 2B von Willebrand's disease: detection of a candidate mutation Ser547Phe. Thrombosis & Haemostasis 75: 363-367.

Savage, DA, Tang, JP, Wood, NAP, Evans, J, Bidwell, JL, Wee, JLK, Oei, AA, Hui, KM (1996) A rapid HLA-DRB1*04 subtyping method using PCR and DNA heteroduplex generators. Tissue Antigens 47: 284-292.

Jack, D, Bidwell, J, Turner, M, Wood, N. (1997) Simultaneous genotyping for all three known structural mutations in the human mannan-binding lectin gene. Human Mutation 9: 41-46.

Culpan, D, Standen, GR, Wood, N, Mazurier, C, Gaucher, C, Bidwell, JL (1997) Rapid mutation screening in Type 2A von Willebrand's disease using universal heteroduplex generators. Brit J Haematol 96: 464-469.

Bowen, D, et al (1997) Genetic diagnosis of Factor V Leiden using heteroduplex technology. Thrombosis and Haemostasis 77: 119-122.

Jackson, HA, Bowen, DJ, Worwood, M (1997) Rapid genetic screening for haemochromatosis using heteroduplex technology. Br J Haematol 98: 856-859.

Tyfield, LA, Stephenson, A, Cockburn, F, Harvie, A, Bidwell, JL, Wood, NAP, Pilz, DT, Harper, P, Smith, I (1997) Sequence variation at the phenylalanine hydroxylase gene in the British Isles. Am J Hum Genet 60: 388-396.

Enayat, MS, Theophilus, BDM, Hill, FGH, Rose, PE, Culpan, D, Bidwell, J, Standen, GR (1998) A new candidate mutation (K755E) causing Type 2A Von Willebrand's disease identified by UHG analysis. Br J Haematol 79:240.

Culpan, D, Goodeve, A, Bowen, DJ, Standen, G, Bidwell, J (1988) Rapid genotypic diagnosis of type 2A von Willebrand's disease by heteroduplex analysis. Clin. Lab. Haem 20: 177-178.

Bowen, DJ, Standen, GR, Mazurier, C, Gaucher, C, Cumming, A, Keeney, S, Bidwell, J (1998) Type 2N von Willebrand disease: rapid genetic diagnosis of G2811A (R854Q), C2696T (R816W), T2701A (H817Q) and G2823T (C858F)—detection of a novel candidate type 2N mutation: C2801T (R854W). Thromb Haemost 80: 32-36.

Morse, HR, Olomolaiye, OO, Wood, NAP, Keen, LJ and Bidwell, JL (1999) Induced heteroduplex genotyping of TNFa, IL-lb, IL-6 and IL-10 polymorphisms associated with transcriptional regulation. Cytokine 11: 789-795.

Wood, NAP, Thompson, SC, Smith, RM, Bidwell, JL (2000) Identification of human TGF-b1 signal (leader) sequence polymorphisms by PCR-RFLP. J Immunol Methods 234: 117-122.

Bidwell, JL, Olomolaiye, OO, Keen, LJ, Wood, NAP, Morse, HR, Laundy, GJ, Thompson, SJ (2000) Cytokine gene polymorphism. In: Human Blood Cells: Consequences of Genetic Polymorphism (Ed. King, M-J), pp. 375-400. Imperial College Press, London.

Wood, NAP, Keen, LJ, Tilley, LA, Bidwell, JL (2001) Determination of cytokine regulatory haplotypes by induced heteroduplex analysis of DNA. J Immunol Meth 249:191-198.

Spink, CF, Keen, LJ, Middleton, PG, Bidwell, JL (2004) Discrimination of suballeles present at the TNFd microsatellite locus using Induced Heteroduplex Analysis. Genes and Immunity 5: 76-79.

Belli et al: "A single, multiplex analysis for all relevant activating NRAS gene mutations using heteroduplex generators." British Journal of Haematology. Aug. 2004, vol. 126, No. 4, p. 602-605.

Belli et al.: "rapid detection of exon 1 NRAS gene mutations using universal heteroduplex generator technology." Human Mutation. Feb. 2003, p. 132-137.

Wang et al: "Effects of bulge composition and flanking sequence on the kinking of DNA by bulged bases." Biochemistry. Feb. 5, 1991, vol. 30. No. 5, p. 1358-1363.

Luebke et al: "Sequence effects on RNA bulge-induced helix bending and a conserved five-nucleotide bulge from the group I introns." Biochemistry. Sep. 10, 1996, vol. 35, No. 36, p. 11677-11684.

Bhattacharyya et al: "The contrasting structures of mismatched DNA sequences containing looped-out bases (bulges) and multiple mismatches (bubbles)." Nucleic Acids Research. Sep. 12, 1989, vol. 17, No. 17, p. 6821-6840.

Nataraj et al: "Single-strand conformation polymorphism and heterduplex analysis for gel-based mutation detection." Electrophoresis. Jun. 1999, vol. 20 No. 6, p. 1177-1185.

European Search Report for related patent application dated Feb. 11, 2010.

European Search Report for related patent application dated Jun. 12, 2009.

* cited by examiner

SEQUENCE LISTING

<160> NUMBER OF SEQ ID NOS: 11

<210> SEQ ID NO 1
<211> LENGTH: 24
<212> TYPE: DNA
<213> ORGANISM: Artificial
<220> FEATURE:
<223> OTHER INFORMATION: Primer for PCR

<400> SEQUENCE: 1
aatccaagac aacactacta aggc                                                 24

<210> SEQ ID NO 2
<211> LENGTH: 20
<212> TYPE: DNA
<213> ORGANISM: Artificial
<220> FEATURE:
<223> OTHER INFORMATION: Primer for PCR

<400> SEQUENCE: 2
ctggatagga ggtcccttac                                                      20

<210> SEQ ID NO 3
<211> LENGTH: 87
<212> TYPE: DNA
<213> ORGANISM: Artificial
<220> FEATURE:
<223> OTHER INFORMATION: Example 1 IHG0

<400> SEQUENCE: 3
aatccaagac aacactacta aggcttgttt gggagaaaaa ggggaagtag ggataggtaa          60
gaggaaagta agggacctcc tatccag                                              87

<210> SEQ ID NO 4
<211> LENGTH: 87
<212> TYPE: DNA
<213> ORGANISM: Artificial
<220> FEATURE:
<223> OTHER INFORMATION: Example 1 IHG1

<400> SEQUENCE: 4
aatccaagac aacactacta aggcttgttt gggagagaaa agggaagtag ggataggtaa          60
gaggaaagta agggacctcc tatccag                                              87

<210> SEQ ID NO 5
<211> LENGTH: 87
<212> TYPE: DNA
<213> ORGANISM: Artificial
<220> FEATURE:
<223> OTHER INFORMATION: Example 1 IHG2

<400> SEQUENCE: 5
aatccaagac aacactacta aggcttgttt gggagaggaa aaggaagtag ggataggtaa          60
gaggaaagta agggacctcc tatccag                                              87

<210> SEQ ID NO 6
<211> LENGTH: 87
<212> TYPE: DNA
<213> ORGANISM: Artificial
<220> FEATURE:
<223> OTHER INFORMATION: Example 1 IHG3

<400> SEQUENCE: 6
aatccaagac aacactacta aggcttgttt gggagaggga aaagaagtag ggataggtaa    60
gaggaaagta agggacctcc tatccag    87

<210> SEQ ID NO 7
<211> LENGTH: 24
<212> TYPE: DNA
<213> ORGANISM: Artificial
<220> FEATURE:
<223> OTHER INFORMATION: TNF Left Primer

<400> SEQUENCE: 7
gttcagcctc cagggtccta caca    24

<210> SEQ ID NO 8
<211> LENGTH: 24
<212> TYPE: DNA
<213> ORGANISM: Artificial
<220> FEATURE:
<223> OTHER INFORMATION: TNF Right Primer

<400> SEQUENCE: 8
gggatttgga aagttgggga caca    24

<210> SEQ ID NO 9
<211> LENGTH: 134
<212> TYPE: DNA
<213> ORGANISM: Artificial
<220> FEATURE:
<223> OTHER INFORMATION: Example 2 IHG0

<400> SEQUENCE: 9
gttcagcctc cagggtccta cacacaaatc agtcagtggc ccagaagacc cccctcagaa    60
tcgaaaagag cagggaggat ggggagtgtg aggggtatcc ttgatgcttg tgtgtcccca    120
actttccaaa tccc    134

<210> SEQ ID NO 10
<211> LENGTH: 134
<212> TYPE: DNA
<213> ORGANISM: Artificial
<220> FEATURE:
<223> OTHER INFORMATION: Example 2 IHG1

<400> SEQUENCE: 10
gttcagcctc cagggtccta cacacaaatc agtcagtggc ccagaagacc cccctcagaa    60
tcggaaaaag cagggaggat ggggagtgtg aggggtatcc ttgatgcttg tgtgtcccca    120
actttccaaa tccc    134

<210> SEQ ID NO 11
<211> LENGTH: 134
<212> TYPE: DNA
<213> ORGANISM: Artificial
<220> FEATURE:
<223> OTHER INFORMATION: Example 2 IHG2

<400> SEQUENCE: 11
gttcagcctc cagggtccta cacacaaatc agtcagtggc ccagaagacc cccctcagaa    60
tcggagaaaa cagggaggat ggggagtgtg aggggtatcc ttgatgcttg tgtgtcccca    120
actttccaaa tccc    134

INDUCED HETERODUPLEX GENERATORS

FIELD OF THE INVENTION

This invention relates to induced heteroduplex generator (IHG) molecules which offer improvements over those known in the art. The invention further relates to methods for the formation of induced heteroduplexes between the improved IHG of the invention and target genomic DNA sequences, and the analysis of such induced heteroduplexes for the genotyping of mutations in animal (e.g. mammalian), plant, viral or bacterial DNA, typically human DNA. The invention may thus be employed, for example, in respect of polymorphisms and mutations within genes associated with inherited genetic disorders (such as for example cystic fibrosis (CFTR gene), phenylketonuria (PAH gene), sickle cell disease and β-thalassaemia (HBB gene)), and also somatic mutations within oncogenes and tumour suppressor genes. The invention also relates to kits comprising the induced heteroduplex generators of the invention, for use in methods of analysing genomic DNA sequences.

BACKGROUND OF THE INVENTION

The ability to detect DNA sequence variances (hereinafter referred to as "polymorphisms" for convenience, but without limitation) in an organism's genome has become an important tool in the diagnosis of diseases and disorders and in the prediction of response to therapeutic regimes. It is becoming increasingly possible, using early variance detection, to diagnose and treat, even prevent the occurrence of, a disease or disorder before it has physically manifested itself. Furthermore, variance detection can be a valuable research tool in that it may lead to the discovery of genetic bases for disorders the cause of which were hitherto unknown or thought to be other than genetic.

Sequence variance can take a number of different forms. For example, a variance can arise through substitution of one or more nucleotides for the same number of others at a particular locus in a gene. Another example would be the deletion of one or more nucleotides from a particular locus in a gene. A still further example would be the insertion of one or more extra nucleotides at a particular locus in a gene. Combinations of substitution, deletion and insertion are also possible. A common type of sequence variance is the single nucleotide polymorphism or SNP. A SNP involves the substitution of one nucleotide for another at a particular locus in a gene. Although each SNP involves only one nucleotide, a single gene may contain numerous SNPs.

Determination of whether a particular gene of a species or of an individual of that species contains a sequence variance is called genotyping. Complete sequencing is, therefore, a method for accomplishing genotyping but it is slow, costly and extremely inefficient.

An alternative genotyping approach known in the art uses makes use of so-called induced heteroduplex generators (previously also termed universal heteroduplex generators and referred to hereinafter by the term "IHG"). These are synthetic DNA sequences that mimic a genomic DNA sequence, but which contain controlled nucleotide substitutions, deletions, insertions or combinations thereof (collectively termed "identifiers") engineered at nucleotide positions opposite to and—in the art—contiguous with (that is immediately adjacent to) known polymorphic sites within the genomic DNA. To detect sequence variances within genomic DNA, the IHG and genomic DNA sequences are amplified separately with the same locus-specific PCR primers and the respective PCR products are subsequently hybridised together by heating and slow cooling in order to generate DNA heteroduplexes. The resulting heteroduplexes are then resolved, e.g. by non-denaturing polyacrylamide minigel electrophoresis. Depending on the number, type and position of the mismatches between the IHG and genomic DNA, different heteroduplexes are generated which migrate at different rates, thus giving rise to characteristic banding patterns for different alleles.

The use of induced heteroduplex generators is discussed in the following references:

1. Bidwell, J L, Clay, T M, Wood, N A P, Pursall, M C, Martin, A F, Bradley, B A and Hui, K M (1993) Rapid HLA-DR-Dw and DP matching by PCR fingerprinting and related DNA heteroduplex technologies. pp 99-116 in: Handbook of HLA Typing Techniques [Eds K M Hui & J L Bidwell] CRC Press: Boca Raton, Fla.
2. Wood, N, Tyfield, L, Bidwell, J (1993) Rapid classification of phenylketonuria genotypes by analysis of heteroduplexes generated by PCR-amplifiable synthetic DNA. Human Mutation 2: 131-137.
3. Bidwell, J L, Wood, N A P, Tyfield, L A, Clay, T M, Culpan, D, Evans, J M, Pursall, M C, Bradley, B A (1993) Universal heteroduplex generators: reagents for genotyping of HLA and of human diseases. Molecular Bases of Human Diseases (Ed. E. E. Polli). pp 27-34. Elsevier/North-Holland, Amsterdam.
4. Wood, N, Standen, G, Hows, J, Bradley, B, Bidwell, J. (1993) Diagnosis of sickle cell disease with a universal heteroduplex generator. Lancet 342: 1519-1520.
5. Bidwell, J L, Wood, N A P, Clay, T M, Pursall, M C, Culpan, D, Evans, J, Bradley, B A, Tyfield, L A, Standen, G, Hui, K M (1994) DNA heteroduplex technology. In: Chrambach, A, Dunn, M J, Radola, B J (Eds), Advances in Electrophoresis, Volume 7, pp 311-351. VCH Press, Weinheim.
6. Clay, T M, Cuplan, D, Howell, W M, Sage, D A, Bradley, B A, Bidwell, J L. (1994) UHG crossmatching: a comparison with PCR-SSO typing in the selection of HLA-DPB1-compatible bone marrow donors. Transplantation 58: 200-207.
7. Bidwell, J L. (1994) Advances in DNA-based HLA-typing methods. Immunology Today 15: 303-307.
8. Tyfield, L A, Stephenson, A, Bidwell, J L, Wood, N A P, Cockburn, F, Harvie, A, Smith, I. (1994) Mutation analysis of the phenylalanine hydroxylase gene using heteroduplex analysis with synthetic DNA constructs. Acta Paediatrica 83: 47-48.
9. Savage, D A, Wood, N A P, Bidwell, J L, Hui, K M. (1995) HLA-DRB1*01 subtyping by heteroduplex analysis. Tissue Antigens 45: 120-124.
10. Wood, N, Standen, G, Murray, E W, Lillicrap, D, Holmberg, L, Peake, I R, Bidwell, J. (1995) Rapid genotype analysis in type 2B von Willebrand's disease using a universal heteroduplex generator. Brit J Haematol 89: 152-156.
11. Wood, N, Standen, G, Old, J, Bidwell, J. (1995) Optimisation and properties of a UHG for genotyping of haemoglobins S and C. Hum Mutation 5: 166-172.
12. Savage, D A, Wood, N A P, Bidwell, J L, Fitches, A, Old, J M, Hui, K M. (1995) Detection of b-thalassaemia mutations using DNA heteroduplex generator molecules. Brit J Haematol 90: 564-571.
13. Tyfield, L A, Zschocke, J, Stephenson, A, Cockburn, F, Harvie, A, Bidwell, J L, Wood, N A P, Hunt, L P. (1995) Discordant phenylketonuria phenotypes in one family: the relationship between genotype and clinical outcome is a function of multiple effects. J Med Genet 32: 132-136.

14. Wood, N A P, Bidwell, J L. (1996) UHG: heteroduplex and universal heteroduplex generator analysis. In: Laboratory protocols for mutation detection (ed Landegren, U), pp 105-112. Oxford University Press for the Human Genome Organisation.
15. Wood, N, Bidwell, J. (1996) Genetic screening and testing by induced heteroduplex formation. Electrophoresis 17: 247-254.
16. Wood, N, Standen, G R, Bowen, D J, Cumming, A, Lush, C, Lee, R, Bidwell, J. (1996) UHG-based mutation screening in type 2B von Willebrand's disease: detection of a candidate mutation Ser547Phe. Thrombosis & Haemostasis 75: 363-367.
17. Savage, D A, Tang, J P, Wood, N A P, Evans, J, Bidwell, J L, Wee, J L K, Oei, M, Hui, K M (1996) A rapid HLA-DRB1*04 subtyping method using PCR and DNA heteroduplex generators. Tissue Antigens 47: 284-292.
18. Jack, D, Bidwell, J, Turner, M, Wood, N. (1997) Simultaneous genotyping for all three known structural mutations in the human mannan-binding lectin gene. Human Mutation 9: 41-46.
19. Culpan, D, Standen, G R, Wood, N, Mazurier, C, Gaucher, C, Bidwell, J L (1997) Rapid mutation screening in Type 2A von Willebrand's disease using universal heteroduplex generators. Brit J Haematol 96: 464-469.
20. Bowen, D, et al (1997) Genetic diagnosis of Factor V Leiden using heteroduplex technology. Thrombosis and Haemostasis 77: 119-122.
21. Jackson, H A, Bowen, D J, Worwood, M (1997) Rapid genetic screening for haemochromatosis using heteroduplex technology. Br J Haematol 98: 856-859.
22. Tyfield, L A, Stephenson, A, Cockburn, F, Harvie, A, Bidwell, J L, Wood, N A P, Pilz, D T, Harper, P, Smith, I (1997) Sequence variation at the phenylalanine hydroxylase gene in the British Isles. Am J Hum Genet 60: 388-396
23. Enayat, M S, Theophilus, B D M, Hill, F G H, Rose, P E, Culpan, D, Bidwell, J, Standen, G R (1998) A new candidate mutation (K755E) causing Type 2A Von Willebrand's disease identified by UHG analysis. Br J Haematol 79:240
24. Culpan, D, Goodeve, A, Bowen, D J, Standen, G, Bidwell, J (1988) Rapid genotypic diagnosis of type 2A von Willebrand's disease by heteroduplex analysis. Clin. Lab. Haem 20: 177-178.
25. Bowen, D J, Standen, G R, Mazurier, C, Gaucher, C, Cumming, A, Keeney, S, Bidwell, J (1998) Type 2N von Willebrand disease: rapid genetic diagnosis of G2811A (R854Q), C2696T (R816W), T2701A (H817Q) and G2823T (C858F)-detection of a novel candidate type 2N mutation: C2801T (R854W). Thromb Haemost 80: 32-36.
26. Morse, H R, Olomolaiye, O O, Wood, N A P, Keen, L J and Bidwell, J L (1999) Induced heteroduplex genotyping of TNFa, IL-1b, IL-6 and IL-10 polymorphisms associated with transcriptional regulation. Cytokine 11: 789-795.
27. Wood, N A P, Thompson, S C, Smith, R M, Bidwell, J L (2000) Identification of human TGF-b1 signal (leader) sequence polymorphisms by PCR-RFLP. J Immunol Methods 234: 117-122.
28. Bidwell, J L, Olomolaiye, O O, Keen, L J, Wood, N A P, Morse, H R, Laundy, G J, Thompson, S J (2000) Cytokine gene polymorphism. In: Human Blood Cells: Consequences of Genetic Polymorphism (Ed. King, M-J), pp 375-400. Imperial College Press, London.
29. Wood, N A P, Keen, L J, Tilley, L A, Bidwell, J L (2001) Determination of cytokine regulatory haplotypes by induced heteroduplex analysis of DNA. J Immunol Meth 249:191-198.
30. Spink, C F, Keen, L J, Middleton, P G, Bidwell, J L (2004) Discrimination of suballeles present at the TNFd microsatellite locus using Induced Heteroduplex Analysis. Genes and Immunity 5: 76-79.
31. Smith A J P, Keen L J, Wood N A P, Elson C J, Bidwell J L (2004) Haplotype analysis of IL1A, IL1B, IL1RN and IL1R1 promoter SNPs. In: HLA 2002. Blackwell Munksgaard, Denmark
32. PhD thesis of NAP Wood dated November 1995 entitled "An Investigation of the Potential of Universal Heteroduplex Generators in Identification of Point Mutations Within DNA", held in the library of the University of Bristol.

WO-A-93/19201 and GB-A-2338062 also relate to genotyping using IHG technology.

The content of the above patent documents and other references is incorporated herein by reference for all purposes.

However, it is to be noted that the content of the above patent documents and other references is not necessarily prior art in every designated state of this PCT patent application, as the prior art status is to be judged according to domestic legislation. Therefore, no admission is made that any particular document referred to herein is prior art to any of the claims presently included in this application, or which may be introduced by future amendment, or which may be included or introduced in any continuation or divisional application, or any other corresponding or further application, which may be filed in the future based on the present PCT patent application.

Whilst genotyping using IHGs is simple to use, may be carried out quickly, and is reliable, it would nevertheless be desirable to improve heteroduplex band resolution, so that the allele-specific patterns are more easily distinguished. This will enable, for example, a shortened gel electrophoresis time.

BRIEF DESCRIPTION OF THE INVENTION

In accordance with the present invention, it has been found that heteroduplex band resolution may be improved by modifying the IHG molecule such that the identifier is spaced apart from the position immediately adjacent to the site of the polymorphism which is to be genotyped. It has unexpectedly been found that, when such modified IHG molecules are used, the resolution of the induced heteroduplexes is significantly improved.

Thus, in accordance with a first aspect of the invention, there is provided an IHG which is a synthetic DNA sequence including at least one nucleotide position which corresponds to a known polymorphic site in a genomic DNA sequence, characterized in that said synthetic DNA sequence includes at least one nucleotide substitution, deletion and/or insertion (herein: "identifier") relative to the genomic sequence at a nucleotide position spaced by a distance of at least one base from the nucleotide position(s) which corresponds to the known polymorphic site and wherein the nucleotide(s) between the nucleotide position which corresponds to the polymorphic site and the nucleotide substitution, deletion and/or insertion are unchanged from the genomic sequence, and wherein, where the genomic sequence includes a plurality of known polymorphic sites, the identifier is spaced by a distance of at least one base from the nucleotide position(s) which correspond to each of the known polymorphic sites.

The IHG molecule according to the invention is preferably adapted for use in detecting one or more known polymorphisms (e.g. genetic mutations) at a known polymorphic site of genomic DNA, and most particularly is adapted for use in an IHG detection method which results in significantly improved resolution of induced heteroduplexes, in terms of the separation of the bands following the step in which the heteroduplexes are resolved, as for example by electrophoresis, in comparison with a corresponding method in which the IHG identifier is not so spaced from the nucleotide position which corresponds to the known polymorphic site.

It will be understood that the expression "known polymorphic site" as used herein refers particularly to a site of polymorphism that is under specific investigation using the IHG molecule. A polymorphic site in a genomic (wild type) DNA sequence is the location in that DNA sequence which corresponds to a site of genetic alteration in a known allelic variant of the gene. Such a site of genetic alteration may be a single base substitution, insertion or deletion, or a contiguous series of two or more substitutions, additions, insertions or combinations thereof.

It will be understood that the expression "nucleotide position" as used herein includes within its scope any relevant locus of a nucleotide sequence, as the context requires, such as, for example, a region of a nucleotide sequence, a locus where a region of a nucleotide sequence has been deleted, a point between regions of a nucleotide sequence, as well as individual bases of a nucleotide sequence.

By way of example, where a polymorphic site comprises, in the allelic variant, a single base alteration, the IHG comprises a single nucleotide position which corresponds to that polymorphic site, and the identifier in the IHG molecule is at least one base removed from this nucleotide positions. Where the polymorphic site comprises a series of three contiguous base alterations, the IHG comprises three contiguous nucleotide positions which correspond to that polymorphic site, and the identifier in the IHG molecule is at least one base removed from this set of three nucleotide positions.

In another example, where the polymorphic site may comprise, in the allelic variant, a single base deletion, the IHG comprises a single nucleotide position which corresponds to that polymorphic site, and the identifier in the IHG molecule is at least one base removed from this nucleotide positions. Where the polymorphic site comprises a series of three contiguous base deletions, the IHG may comprise three contiguous nucleotide positions which correspond to that polymorphic site, and the identifier in the IHG molecule is at least one base removed from this set of three nucleotide positions.

In a still further example, where the polymorphic site may comprise, in the allelic variant, a single base insertion, the IHG comprises a pair of nucleotide positions which span the polymorphic site, and the identifier in the IHG molecule is at least one base removed from these nucleotide positions. Where the polymorphic site comprises a series of three contiguous base insertions, the IHG may comprises five nucleotide positions which span that polymorphic site, and the identifier in the IHG molecule is at least one base removed from this set of three nucleotide positions.

The polymorphic site may comprise a combination of contiguous substitutions, insertions or deletions. In all cases, the identifier is spaced by at least one base from the set of nucleotide positions which correspond to the contiguous elements of the polymorphic site. In accordance with a second aspect of the present invention, there is provided a method for the formation of induced heteroduplexes between a target gene sequence and an IHG molecule corresponding to said target gene sequence, said method comprising:

(a) providing a population of the IHG molecule;

(b) providing a population of the target gene sequence; and (c) combining the respective populations of (a) and (b) under conditions suitable for heteroduplex formation;

wherein the IHG molecule is according to the first aspect of the present invention.

The populations of the IHG molecule and the target gene sequence may be provided by amplifying the IHG and the target gene sequence. One suitable well known amplification method is PCR.

In this method aspect of the present invention, the induced heteroduplexes may then be resolved on a suitable support, as for example by electrophoresis, and then analysed to determine the genotype of the target gene sequence. The resolution of the induced heteroduplexes formed according to the present invention, in particular the separation of the bands following the step in which the heteroduplexes are separated as, for example, by electrophoresis, is found to be improved, preferably significantly improved, in comparison with a corresponding method in which the IHG identifier is not so spaced from the nucleotide position which corresponds to the known polymorphic site.

In accordance with a third aspect of the present invention, there is provided the use of an IHG molecule according to the first aspect of the present invention for providing improved resolution of induced heteroduplexes on a suitable support, for example by electrophoresis, in comparison with a corresponding method in which the IHG identifier is not so spaced from the nucleotide position which corresponds to the known polymorphic site. The improved resolution may be an improved separation of the bands corresponding to the heteroduplexes on the support.

The method of the present invention may thus be used to predict the likelihood that a human subject will be susceptible to a particular genetic condition or disorder associated with the polymorphism for which the IHG is designed. In another aspect, therefore, the invention relates to a method for predicting the presence, absence, likelihood of the presence or absence, or severity of a particular condition or disorder associated with a particular genotype. In such methods, a nucleic acid sample is obtained from an individual and if necessary the nature of the polymorphic site is investigated to the required level of understanding. This will typically require that the presence or absence of one particular base or sequence of bases can be correlated with a specified genetic disorder or condition. An IHG according to the first aspect of the invention can then be constructed, based on the knowledge of the polymorphic site in the genomic DNA sequence. Using this IHG, the method according to the second aspect of the invention is performed, and/or the IHG is used in accordance with the third aspect of the invention, and the resolved induced heteroduplexes analysed to predict the presence, absence, likelihood of the presence or absence, or severity of a particular condition or disorder in the individual.

According to a fourth aspect of the present invention, there is provided a kit comprising an IHG according to the first aspect of the present invention, forward and reverse primers for the IHG, and optionally a control DNA sequence and instructions for use.

BRIEF DESCRIPTION OF THE DRAWINGS

The attached figures are provided purely for illustration and without limiting the scope of the invention.

DETAILED DESCRIPTION OF THE INVENTION

Figure 1:
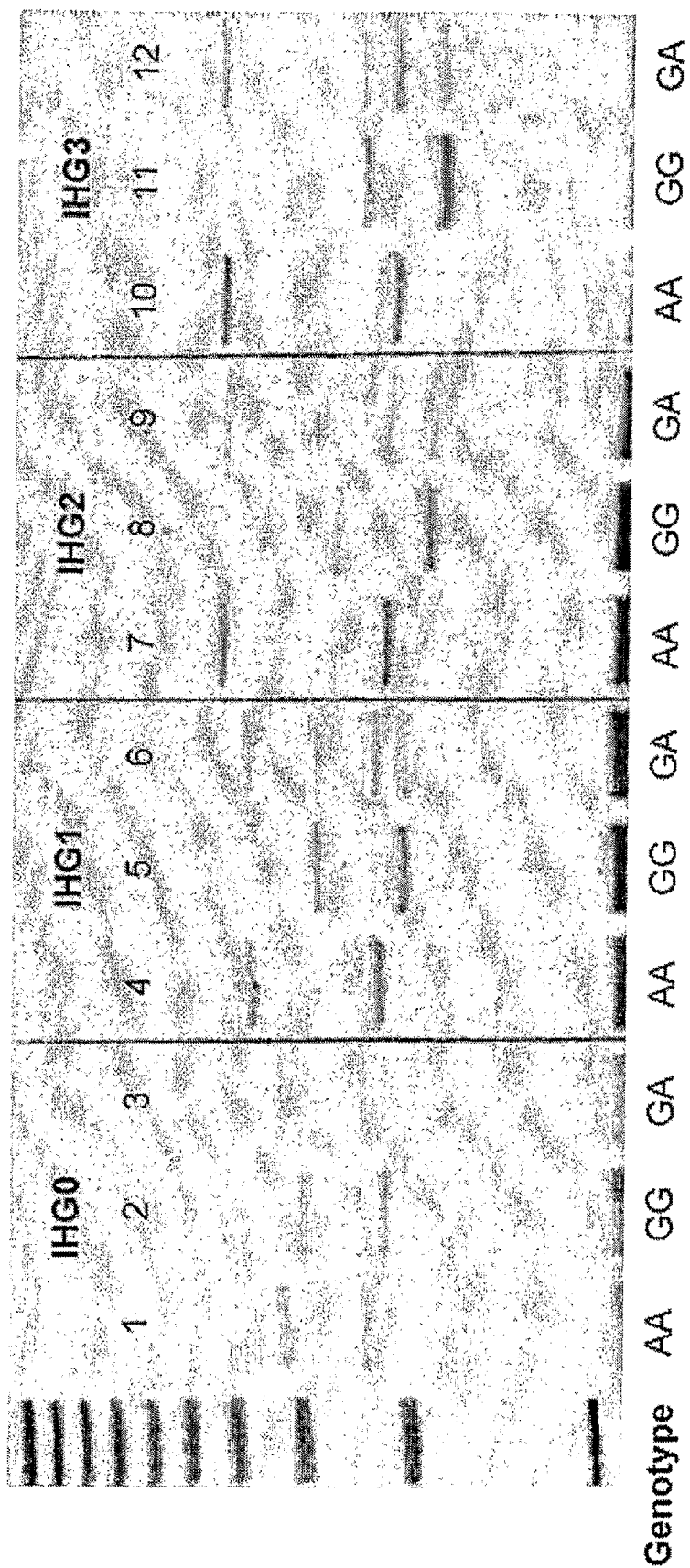
FIG. 1 illustrates the heteroduplex patterns obtained using an IHG of the prior art (IHG0) and IHGs of the invention (IHG1, IHG2, and IHG3), in the genotyping of the "−1082" polymorphism in the promoter of the IL-10 gene.

According to the invention, the synthetic DNA sequence includes at least one nucleotide substitution, deletion and/or insertion relative to the genomic sequence at a nucleotide position spaced by a distance of at least one base from the nucleotide position which corresponds to the known polymorphic site and wherein the nucleotide(s) between the nucleotide position which corresponds to the polymorphic site and the nucleotide substitution, deletion and/or insertion are unchanged from the genomic sequence. Where the genomic sequence includes a plurality of known polymorphic sites, the identifier is spaced by a distance of at least one base from the nucleotide position(s) which correspond to each of the known polymorphic sites.

The spacing of the nucleotide substitution, deletion and/or insertion from the nucleotide position which corresponds to the known polymorphic site is preferably up to about ten bases, more preferably up to about eight bases, e.g. from 1 to about 6 bases, most particularly any number selected from 1, 2, 3, 4, 5 or 6 bases. In the case where there are two or more known polymorphic site, the preferred spacing of up to 10 bases is in relation to the polymorphic site which is closest to the identifier.

In accordance with one embodiment of this invention, genetic material of a subject, normally a human subject, is analysed to determine its genotype with respect to a particular single nucleotide polymorphism (SNP) at a specific location of a gene. The gene which includes the SNP has at least two alleles, which are referred to here as the reference allele and the variant allele. The reference allele (prototypical or wild type allele) has been designated arbitrarily and typically corresponds to the nucleotide sequence of the gene which has been deposited with GenBank or TIGR under a given accession number. The variant allele contains a variant nucleotide (that is a different nucleotide to that of the reference allele) at the SNP site or at each of the SNP sites in the gene.

In genotyping using IHG technology, a sample of nucleic acid is obtained from the subject, and the gene segment containing the polymorphic site is amplified to provide a population of amplicons bearing the sequence of the gene segment. Typically, this amplification of the gene segment is accomplished by PCR using a pair of primers which flank the said gene segment. Suitable primers are selected which are specific for the gene segment under consideration. Primers are selected to amplify a gene segment which is of the order of from 90 to 400 bases in length, and preferably of the order of 100 to 150 base pairs in length. It is normally preferred that the polymorphic site is located in the central region of the gene segment, that is to say approximately in the central third of the gene segment. PCR amplification of the gene segment will result in a population of double stranded amplicons, as is well known. More details of the procedure which may be used for PCR amplification can be found in WO 93/19201.

Where the nucleic acid under examination is mammalian genomic DNA, a sample of the DNA is obtained from an individual or other object whose genotype for a specific characteristic it is wished to study. (The term "individual" is intended to include a foetus.) DNA can be extracted from all nucleated cells. Typically, the DNA is obtained from peripheral blood cells for convenience. Foetal DNA can be obtained from placental cells or amniotic fluid. Other sources of DNA include hair follicles, mummified bodies, etc. The DNA may be isolated by any appropriate method, for example by the rapid salting out method described by Miller et al (Miller, S., Dykes, D. and Polesky, H. (1988) "A simple salting out procedure for extracting DNA from human nucleated cells"; Nucl. Acids Res. 16:1215). Alternatively, the DNA may be isolated as cDNA from mRNA by reverse transcription.

A population of an IHG molecule which has a sequence corresponding to the gene segment, but modified as discussed herein to include controlled nucleotide substitution, deletion, insertion or combination thereof is also provided. Typically, the IHG population is prepared by amplification using, for example PCR. Again, more details of the procedure which may be used for PCR amplification can be found in WO 93/19201. The primers chosen for the PCR are selected to provide amplification of the IHG molecule. PCR amplification will result in a population of double stranded IHG amplicons. The IHG may preferably be substantially identical in length to the gene segment under consideration (disregarding any necessary inserted or deleted bases of the IHG), or may be a different length, for example shorter than or longer than the gene segment. However, if the gene segment and IHG are of different length (disregarding any necessary inserted or deleted bases of the IHG), there must be a sufficient degree of overlap to permit heteroduplex formation between the amplified populations of the gene segment and the IHG. The primers used in amplifying the IHG and the gene segment respectively may be the same or different. Typically, however, the same primers are used, resulting in amplified IHG and gene segment which are of substantially the same length (disregarding any necessary inserted or deleted bases in the IHG). As taught in WO 93/19201, the primers may be labelled.

PCR amplification of the gene segment and the IHG may be accomplished in the same or separate vessels ("mixed" or "separate" PCR respectively). It is preferred to conduct amplification separately and then to combine or pool the amplified populations of the gene segment and the IHG in order to permit heteroduplex formation to proceed.

Heteroduplex formation between the combined populations of IHG and the gene segment which contains the polymorphic site is accomplished by first heating the combined population of IHG and gene segment in order to separate the double stranded DNA into single stranded DNA and then cooling to permit heteroduplex formation, as described for example in WO-A-93/19201.

The heteroduplexes formed are separated according to their molecular conformation which affects their apparent, but not actual, molecular weight. This may be achieved by, for example, electrophoresis. The separation is typically effected on a gel which does not fully denature the nucleic acid, such as a non-denaturing polyacrylamide gel. Electrophoresis is conducted under conditions which effect a desired degree of resolution of the duplexes. A degree of resolution that separates duplexes that differ in "apparent size"—resulting from their different molecular conformations—by as little as about 10 bp is usually sufficient. Size markers may also be run on the gel to permit estimation of the mobility and thus the apparent size of duplexes. In addition, or alternatively, a control DNA molecule having a sequence which corresponds to the known allele of the gene under consideration can also be separately amplified using PCR and allowed to form heteroduplexes with the IHG being used, with the resultant sample then being run on the gel to provide markers on the gel for the different heteroduplexes which result.

The distribution, i.e. the resolution pattern, of the heteroduplexes will be allele-specific. This resolution pattern or PCR fingerprint can next be visualised. Where the PCR primers have been labelled, this label may be revealed. A substrate carrying the separated labelled duplexes is contacted with a reagent which detects the presence of the label. Where the PCR primers were not labelled, the substrate bearing the PCR fingerprint may be contacted with, for example, ethidium bromide or SYBR™ green (available from Molecular Probes) and the nucleic acid fragments visualised under ultraviolet light; alternatively, the heteroduplexes may be visualised with silver staining.

The above discussion represents a general summary of how the technique of genotyping using IHG technology may proceed, in a manner which is well known in the art. The present invention offers an improvement in the known methodology by providing a modified IHG molecule in which the so-called "identifier" is shifted away from the position which corresponds to the polymorphic site under investigation. As previously stated, the DNA sequence of the IHG is modified to include at least one nucleotide substitution, deletion and/or insertion at a nucleotide position separated by a distance of at least one base from the nucleotide position which corresponds to the known polymorphic site, nucleotide(s) at positions between the nucleotide position which corresponds to the polymorphic site and the nucleotide substitution, deletion and/or insertion being unchanged from the genomic sequence.

The IHG molecule may be provided either as a double stranded or a single stranded DNA molecule. If the molecule is less than about 150 bp in length, it is preferable for single stranded DNA to be used. In the following discussion, the expressions "base" and "base pair" are both used; they are not intended to refer strictly to only one of the single or double stranded forms of the IHG, but are applicable, with appropriate modification understood, to either form. In the methods according to the invention, the initial molecule is amplified, for example using PCR. By convention, and as used herein, the sequence of the "coding" strand of the IHG is referred to. In an IHG, the "coding" strand corresponds to the coding strand of the genomic DNA which the IHG has been designed to mimic. By "corresponds" is meant that the IHG has the sequence of the genomic DNA which the IHG has been designed to effectively mimic, save for the deliberate deletion, substitution and/or insertion which creates a deliberate mismatch and thus leads to the formation of induced heteroduplexes). It will be noted in particular that exact hybridisable conformity between the sequences of the IHG and the genomic DNA outside the regions of interest for operation of the present invention is not essential, and the invention is not so limited. A workable system will still be achieved if there are differences in the relative sequences between the IHG and the genomic DNA. Indeed, in some circumstances, it may be desirable to create deliberate mismatches between the IHG and the genomic DNA, for example to produce particular desired effects in the resolution of the resultant heteroduplexes. Such deliberate mismatching will not, of course, be so great as to prevent effective hybridisation to form the heteroduplex.

In the IHG, the nucleotide at the position corresponding to the polymorphic site may be the same as the nucleotide of the wild type genomic DNA or the same as the allelic variant.

The present invention may be adapted to probe for more than one polymorphic site in a given gene segment. Thus, for example where a gene segment includes two or more polymorphic sites which are relatively close to each other (for example within about 300 base pairs of each other), the IHG may be designed to identify the different allelic combinations and may thus include an "identifier" sequence in respect of each polymorphic site. Where the IHG includes two or more sites where a deliberate mismatch is created, the number of possible patterns of heteroduplex bands will increase, but in principle the band pattern for any combination of alleles can be analysed and interpreted by the use of suitable control data.

Where the identifier is a base pair deletion and the IHG is designed to include a single mismatch site, the deletion may be a single deletion or a series of base pair deletions with respect to the genomic DNA sequence. Typically, the length of deleted DNA is from 1 to about 10 base pairs, for example from about 2 to about 6 base pairs.

Where the identifier is a base pair substitution and the IHG is designed to include a single mismatch site, the substitution may be a single substitution or a series of base pair substitutions with respect to the genomic DNA sequence. Typically, the length of substituted DNA is from 1 to about 10 base pairs, for example from about 2 to about 6 base pairs.

Where the identifier is a base pair insertion and the IHG is designed to include a single mismatch site, the insertion may be a single insertion or a series of base pair insertion with respect to the genomic DNA sequence. Typically, the length of inserted DNA is from 1 to about 10 base pairs, for example from about 2 to about 6 base pairs.

Where the IHG includes two or more mismatch sites, each identifier is at least one base pair in length and typically between 1 and about 5 base pairs, e.g. about 2 or 3, base pairs in length. The combined length of deletion, substitution or insertion amongst the two or more identifiers may be up to 10% of the total length of the genomic target, and typically is about 3% of the total length of the target.

The identifier may also be composed of a combination of deletion, substitution or insertion relative to the genomic sequence.

It is presently preferred that the modification is a base pair insertion. The preferred insertion is a sequence of the same base, for example a series of A or G nucleotides, most preferably a series of A nucleotides. However, the insertion may be a combination of different bases.

The IHG molecules of the present invention may be synthesised by methods well known in the art, as for example discussed in WO 93/19201.

EXAMPLES OF THE INVENTION

Example 1

This example demonstrates the use of the present invention to detect the −1082 polymorphism in the IL-10 gene.

The following primer sequences for the −1082 polymorphism PCR were as follows:

```
Forward primer:    AATCCAAGACAACACTACTAAGGC

Reverse primer:    CTGGATAGGAGGTCCCTTAC
```

A first IHG (IHG0) in accordance with the prior art was synthesised having the sequence:

```
IHG0
AATCCAAGACAACACTACTAAGGCTTGTTTGGGAGA*AAAAGGG

GAAGTAGGGATAGGTAAGAGGAAAGTAAGGGACCTCCTATCCAG
```

The "A" residue shown in bold and indicated by an asterisk (*) is the position of the polymorphism. The string of four "A" residues which are shown underscored represent a sequence of inserted residues which serve as the "identifier".

IHG molecules in accordance with the invention were also synthesized as follows:

```
IHG1
AATCCAAGACAACACTACTAAGGCTTGTTTGGGAGA*GAAAAGG

GAAGTAGGGATAGGTAAGAGGAAAGTAAGGGACCTCCTATCCAG

IHG2
AATCCAAGACAACACTACTAAGGCTTGTTTGGGAGA*GGAAAAG

GAAGTAGGGATAGGTAAGAGGAAAGTAAGGGACCTCCTATCCAG

IHG3
AATCCAAGACAACACTACTAAGGCTTGTTTGGGAGA*GGGAAAA

GAAGTAGGGATAGGTAAGAGGAAAGTAAGGGACCTCCTATCCAG
```

IHG1, IHG2, and IHG3 have identical sequence to IHG0, except the sequence of four identifying 'A' residues has been moved 1, 2, or 3 bases away (to the right as shown) from the polymorphic site respectively.

PCR amplifications were carried out in a total reaction volume of 20 µl, containing 10 ng genomic DNA or IHG, 0.5U Taq polymerase (Advanced Biotechnologies), 5 µM of each primer (forward and reverse), 1.5 mM MgCl2, 200 µM of each dNTP, 67 mM Tris-HCl (pH 8.8), 16 mM (NH4)2SO4 and 0.01% Tween. The PCR was optimised on an MJ-PTC-100 thermal cycler (GRI, Braintree, UK). The PCR parameters for both genomic DNA and IHGs were as follows: initial denaturation for 5 min at 95° C., followed by 32 cycles of 95° C. for 30 sec, 55° C. for 1 min, 72° C. for 30 sec with a final extension of 72° C. for 5 min.

The PCR products were combined and cross-matched.

Cross-matching parameters were 95° C. for 2 min, followed by an initial controlled cooling step to 65° C. (ramping rate=1.0° C./s) and holding for 1 min. A second controlled cooling step was inserted to 45° C. (ramping rate=0.1° C./s) and held for 1 min, with a final holding step at 6° C.

Heteroduplexes were resolved on a nondenaturing 15% Protogel® polyacrylamide gel (National Diagnostics, Hull, UK) using a 'triple wide' minigel system (30 cm×8 cm; CBS Scientific Company, Del Mar, USA): gel constitution 37.5:1 (w/v acrylamide:bisacrylamide). Electrophoresis was carried out at 300V for 90 min. The gel was post-stained in 1× Tris borate EDTA (TBE) buffer containing 0.5 µg·ml ethidium bromide and examined using a 302 nm UV transilluminator. Images for analysis were acquired using an EDAS 120 system (Kodak).

The results obtained are shown in FIG. 1. It can be seen that there is improved separation of heteroduplex bands when the identifier is moved away from the polymorphism, rather than if placed immediately adjacent to the polymorphic site (i.e. with IHG1, IHG2 and IHG3). The resulting increased separation of heteroduplex bands through polyacrylamide gel allows identification of alleles within a shortened gel electrophoresis time, as the allele-specific patterns are more easily distinguishable. In this experiment, optimal separation of bands, and distinction of allele-specific patterns, is obtained with IHG2.

Example 2

This example demonstrates the use of the present invention to detect the Tumour Necrosis Factor (TNF) gene promoter −238 polymorphism. The same experimental procedure as for Example 1 was used with the following primers and IHG molecules:

```
TNF Left Primer: GTTCAGCCTCCAGGGTCCTACACA

TNF Right Primer GGGATTTGGAAAGTTGGGGACACA

IHG0
GTTCAGCCTCCAGGGTCCTACACACAAATCAGTCAGTGGCCCAGA

AGACCCCCCTCAGAATCG*AAAAGAGCAGGGAGGATGGGGAGTGT

GAGGGGTATCCTTGATGCTTGTGTGTCCCCAACTTTCCAAATCCC
```

The "G" residue shown in bold and indicated by an asterisk (*) represent the position of the −238 SNP in TNF. The string of four "A" residues which are shown underscored represent a sequence of inserted residues which serve as the "identifier".

IHG molecules in accordance with the invention were also synthesized as follows:

```
IHG1
GTTCAGCCTCCAGGGTCCTACACACAAATCAGTCAGTGGCCCAGA

AGACCCCCCTCAGAATCG*GAAAAAGCAGGGAGGATGGGGAGTGT

GAGGGGTATCCTTGATGCTTGTGTGTCCCCAACTTTCCAAATCCC

IHG2
GTTCAGCCTCCAGGGTCCTACACACAAATCAGTCAGTGGCCCAGA

AGACCCCCCTCAGAATCG*GAGAAAACAGGGAGGATGGGGAGTGT

GAGGGGTATCCTTGATGCTTGTGTGTCCCCAACTTTCCAAATCCC
```

IHG1 and IHG2 have identical sequence to IHG0, except the sequence of four identifying 'A' residues has been moved 2 or 3 bases away (to the right as shown) from the polymorphic site respectively.

Cross-matching parameters were 95° C. for 2 min, followed by an initial controlled cooling step to 65° C. (ramping rate=1.0° C./s) and holding for 1 min. A second controlled cooling step was inserted to 45° C. (ramping rate=0.1° C./s) and held for 1 min, with a final holding step at 6° C.

Figure 2:
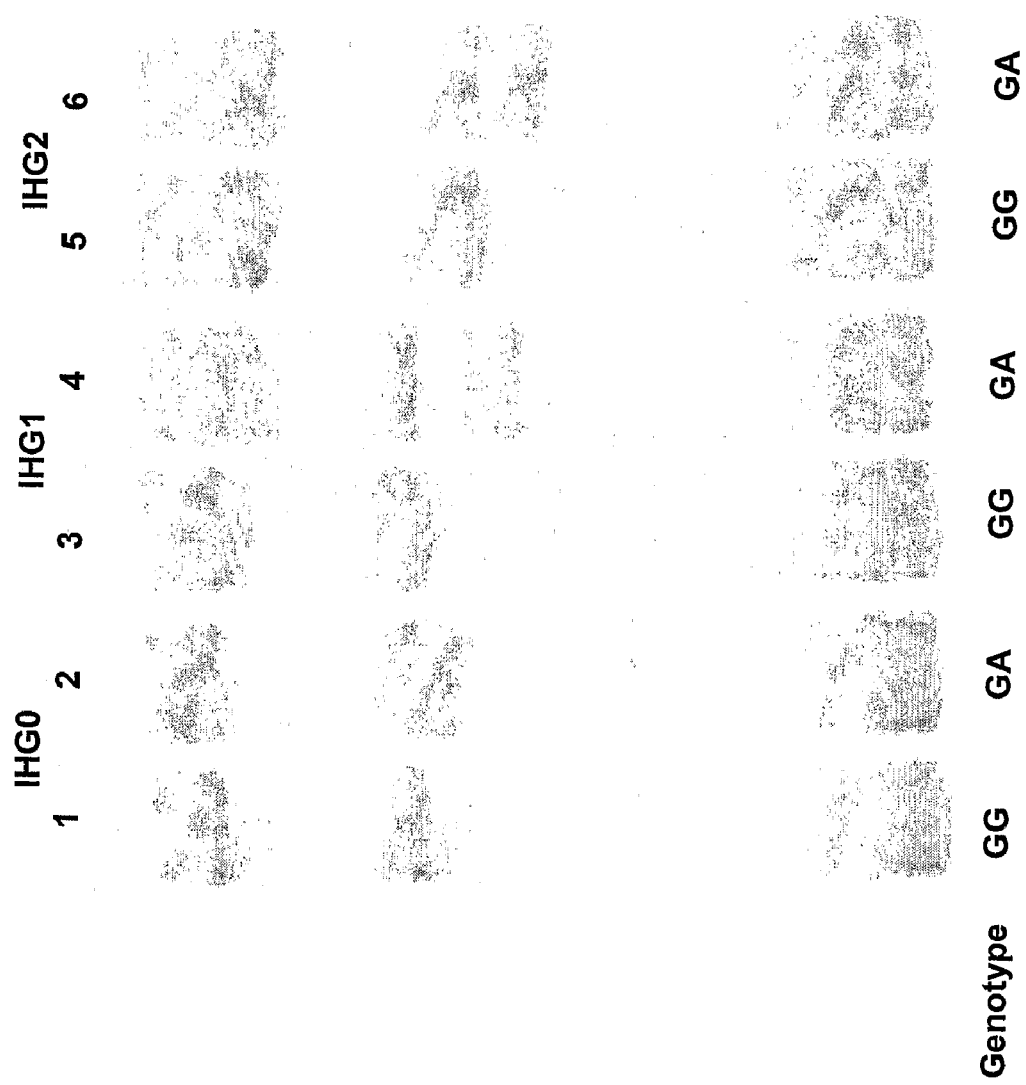
FIG. 2 illustrates the heteroduplex patterns obtained using an IHG of the prior art (IHG0) and IHGs of the invention (IHG1 and IHG2), in the genotyping of the "−238" polymorphism in the Tumour Necrosis Factor (TNF) gene promoter.

FIG. 2 shows the results of cross-matching two genomic DNA samples, one being the GG variant and the other being the GA variant with the three different IHG reagents. Two of the three possible genotypes at this locus are shown. Lanes 1 and 2 show the results of cross-matching the two genomic DNA samples with IHG0—this IHG reagent has an identifier consisting of 4 'A' residues located immediately adjacent to the polymorphic site. Lanes 2-3 and 4-5 show the heteroduplex banding patterns obtained when the same two genomic DNA samples are cross-matched with IHG1 and IHG2 (with identifiers located 2 and 3 bases away from the polymorphic site respectively). The results show that moving the identifying 'A' residues 2 bases away from the polymorphic site has a beneficial effect, with more readily distinguishable allele-specific banding patterns obtained following cross-matching with IHG1 as compared to IHG0. A further increase in separation of bands is not seen when the identifier is moved to 3 bases away form the site of the polymorphism. Optimal separation in this case is obtained with IHG1.

The foregoing broadly describes the present invention without limitation. Variations and modifications as will be readily apparent to those of ordinary skill in this art are intended to be included within the scope of this application and subsequent patents.

The invention claimed is:

1. A method for genotyping a target gene sequence said target gene sequence being selected from the group consisting of a −1082 polymorphism in the promoter of the IL-10 gene and a −238 polymorphism in the tumor necrosis factor (TNF) gene promoter comprising:
   (a) providing a population of induced heteroduplex generator (IHG) molecules corresponding to said target gene sequence, the IHG molecule being a synthetic DNA sequence including at least one nucleotide position which corresponds to a known polymorphic site in the genomic DNA sequence of the target gene sequence and a nucleotide insertion ("identifier") relative to the genomic sequence at a nucleotide position spaced by a distance of at least one base from the nucleotide position which corresponds to the known polymorphic site and wherein the nucleotide(s) between the nucleotide position which corresponds to the polymorphic site and the identifier are unchanged from the genomic sequence; wherein the at least one identifier comprises an insertion of a base and the IHG molecule is selected to provide improved separation of a resolved plurality of bands by a method comprising comparing the separation obtained using the IHG molecule with the separation obtained using a corresponding IHG in which the identifier is not so spaced;
   (b) providing a population of the target gene sequence;
   (c) combining the respective populations of (a) and (b) under conditions suitable for heteroduplex formation, to obtain induced heteroduplexes between the target gene sequence and an IHG molecule corresponding to said target gene sequence;
   (d) resolving the induced heteroduplexes into bands on a suitable support; and
   (e) analysing the resolved induced heteroduplexes to determine the genotype of the target gene sequence.

2. A method according to claim 1, wherein the polymorphic site in the genomic DNA sequence is a single nucleotide polymorphism (SNP).

3. A method according to claim 1, wherein the at least one identifier included in the synthetic DNA relative to the genomic sequence comprises an insertion of more than one base.

4. A method according to claim 1, wherein the at least one identifier included in the synthetic DNA relative to the genomic sequence consists of an insertion of one base.

5. A method according to claim 1, wherein the at least one identifier included in the synthetic DNA relative to the genomic sequence consists of an an insertion of more than one base.

6. A method according to claim 1, wherein the genomic sequence includes a plurality of known polymorphic sites and the identifier is spaced by a distance of at least one base from the nucleotide position(s) which correspond to each of the known polymorphic sites.

7. A method according to claim 1, wherein the insertion is a series of identical bases.

8. A method according to claim 7, wherein the identical bases are A nucleotides.

9. A method according to claim 7, wherein the identical bases area G nucleotides.

10. A method according to claim 7, wherein the synthetic DNA sequence is single stranded.

11. A method according to claim 1, wherein the synthetic DNA sequence is double stranded.

12. A method according to claim 1, wherein the synthetic DNA sequence is substantially identical in length to a gene segment of the genomic DNA under consideration, disregarding any inserted or deleted bases of the IHG.

13. A method according to claim 1, wherein the synthetic DNA sequence is a different length than a gene segment of the genomic DNA under consideration, disregarding any inserted bases of the IHG.

14. A method according to claim 1, wherein the resolving of the induced heteroduplexes is performed using electrophoresis.

* * * * *